(12) United States Patent
Spriggs et al.

(10) Patent No.: US 8,456,631 B2
(45) Date of Patent: Jun. 4, 2013

(54) APPARATUS AND METHOD OF PRODUCING A LIGHT BEAM FOR AN OPTICAL MEASUREMENT INSTRUMENT

(75) Inventors: David Michael Spriggs, Malvern (GB); David Anthony Stringfellow, Malvern (GB)

(73) Assignee: Malvern Instruments, Ltd., Malvern (GB)

( * ) Notice: Subject to any disclaimer, the term of this patent is extended or adjusted under 35 U.S.C. 154(b) by 312 days.

(21) Appl. No.: 12/670,535

(22) PCT Filed: Jun. 30, 2008

(86) PCT No.: PCT/GB2008/002237
§ 371 (c)(1),
(2), (4) Date: Aug. 24, 2010

(87) PCT Pub. No.: WO2009/013452
PCT Pub. Date: Jan. 29, 2009

(65) Prior Publication Data
US 2010/0315636 A1    Dec. 16, 2010

(30) Foreign Application Priority Data

Jul. 26, 2007  (GB) .................................. 0714563.4
Sep. 10, 2007  (GB) .................................. 0717521.9

(51) Int. Cl.
*G01N 15/02*    (2006.01)
*G01N 21/00*    (2006.01)

(52) U.S. Cl.
USPC .......................................... 356/336; 356/337

(58) Field of Classification Search
USPC .................................... 356/336, 337
See application file for complete search history.

(56) References Cited

U.S. PATENT DOCUMENTS

| 5,610,712 | A  | * | 3/1997  | Schmitz et al. ............... 356/335 |
| 5,619,324 | A  |   | 4/1997  | Harvill |
| 5,844,685 | A  |   | 12/1998 | Gontin |
| 6,104,489 | A  | * | 8/2000  | Larsson et al. ................ 356/335 |
| 6,456,376 | B1 |   | 9/2002  | Liphardt |
| 7,667,832 | B2 | * | 2/2010  | Backman et al. ............. 356/128 |
| 8,014,069 | B2 | * | 9/2011  | Spilman et al. .......... 359/489.01 |
| 2009/0040602 | A1 | * | 2/2009 | Spilman et al. ............... 359/386 |

FOREIGN PATENT DOCUMENTS

| JP | H08-226895 | 9/1996 |
| JP | H08-511347 | 11/1996 |
| WO | WO 94/02976 | 12/1994 |

* cited by examiner

*Primary Examiner* — Roy M Punnoose
(74) *Attorney, Agent, or Firm* — Kristofer E. Elbing

(57) ABSTRACT

An apparatus for providing a light beam for use in a diffraction instrument (1) includes a device (10; 17; 28) for generating a light beam; and means (12, 21; 24) for shaping the light beam generated by the device (10; 17; 28), dimensioned, in use, to determine the beam shape, and including: an aperture (21; 25) and means (13; 24) for rejecting spatial frequency components above a certain range in the light beam. The apparatus further includes a spatial low-pass filter (14; 15; 26; 27) arranged to filter a beam provided by the beam shaping means.

14 Claims, 7 Drawing Sheets

APPARATUS AND METHOD OF PRODUCING A LIGHT BEAM FOR AN OPTICAL MEASUREMENT INSTRUMENT

This application is a US national phase application under 35 USC §371, and claims priority to PCT patent application number PCT/GB2008/002237 having an international filing date of Jun. 30, 2008, which, in turn, claims priority to United Kingdom patent application number GB 0714563.4 having a filing date of Jul. 26, 2007 and to United Kingdom patent application number GB 0717521.9 having a filing date of Sep. 10, 2007, all three of which are herewith incorporated by reference.

The invention relates to an apparatus for providing a light beam for use in an optical measurement instrument, including a device for generating a light beam; and means for shaping the light beam generated by the device, dimensioned, in use, to determine the beam shape, and including: an aperture and means for rejecting spatial frequency components above a certain range in the light beam.

The invention also relates to a method of providing a light beam in an optical measurement instrument, including generating a light beam; and passing the light beam through a passage dimensioned to determine the beam shape and removing spatial frequency components above a certain range from the light beam.

The invention also relates to a light scattering instrument for determining particle sizes by scattering of light, including an apparatus for providing a light beam to illuminate a particle sample.

Examples of such an apparatus, method and instrument are known. U.S. Pat. No. 5,610,712 describes a conventional pinhole-based spatial filter, which generally includes: a light generating laser diode, the beam of which is passed through a first circular beam stop which acts to eliminate unwanted peripheral light rays and makes the light beam circular in shape, focusing lenses, a pinhole member and a second beam stop to remove diffraction rings caused by parts of the beam hitting the edges of the pinhole. Finally, the laser light beam is collimated by a lens and passed on into a sample containing cell.

A problem of the known set-up is that it is sensitive to misalignment of the pinhole member and the beam emerging from the laser diode, in the sense that misalignment can lead to significant deterioration of the spatial coherence of the resulting light beam.

It is an object of the invention to provide an apparatus, method and instrument of the types mentioned in the opening paragraphs resulting in relatively well-collimated beams of light in the face of misalignments and tolerance spreads of components of the means for shaping the light beam from the device generating it.

This object is achieved by the apparatus according to the invention, which further includes a spatial low-pass filter arranged to filter a beam provided by the beam shaping means, and is characterized in that the spatial low-pass filter includes a relay lens arrangement functioning as a Fourier transform lens and an aperture plate positioned generally in a focal plane of the relay lens arrangement.

Somewhat counter-intuitively, it has been found that increasing the number of optical components by adding the second spatial filter actually makes the resulting apparatus less sensitive to misalignment and tolerances, in particular of the aperture. Where the means for shaping the light beam include a combination of a pinhole and a beam stop, misalignments of the pinhole relative to the light beam and/or the beam stop become less critical. Moreover, the pinhole need not be extremely small to achieve a good separation of spatial frequency components, making the apparatus easier to manufacture and providing for greater light throughput.

It is noted that U.S. Pat. No. 5,610,712 further discloses a method for determining the respective sizes and size distribution of a plurality of particles disposed in a sample, which method comprises passing a laser beam through a monomode optical fibre to produce at one end of the fibre a point source of light having a high degree of coherence. The fibre must be sufficiently long so that the extraneous light travelling through the cladding of the fibre is attenuated to the extent that it is not detrimental to the output of a clean, spatially filtered beam. In a described embodiment, a six-meter length of optical fibre cable is wrapped in a coil around a cylindrical tube to provide a relatively small, compact assembly, which is thereafter covered by a shrink-wrap cover. There is no disclosure of a spatial low-pass filter arranged to filter a beam provided by the beam shaping means.

The apparatus according to the invention provides a relatively good beam quality, because a beam with an intensity distribution corresponding to a Bessel function and having low-intensity side lobes will emerge from the aperture of a monomode optical fibre (see e.g. Neumann, E.-G., "Single mode fiber fundamentals", Springer, 1988, pp. 202-203). Applying the invention, the presence of the spatial low-pass filter downstream in the direction of propagation will still have an effect, even if the cut-off point of the filter that is the optical fibre and that of the spatial low-pass filter are the same. A further effect achieved in case the beam shaping means comprise a monomode optical fibre is that degradation of the fibre end is compensated for. The optical fibre end must have a super-fine polish to achieve a beam of adequate quality. However, the end face of the optical fibre is susceptible to environmental degradation. This would adversely affect the repeatability of measurements.

The spatial low-pass filter includes a relay lens arrangement, functioning as a Fourier transform lens, and an aperture plate, positioned generally in a focal plane of the relay lens arrangement.

An effect is to allow the apparatus to be made relatively compact and to provide it with a relatively high light output. The relay lens arrangement improves the numerical aperture of the beam, thus reducing the need to resort to a smaller aperture of the beam shaping means. Smaller apertures of the beam shaping means should be avoided, because the circularity of the aperture becomes more critical to the beam quality, and the light throughput is also reduced. Because the relay lens arrangement increases the numerical aperture of the beam passing through it, it also shortens the length of the subsequent optics.

In a variant, the relay lens arrangement includes an assembly of multiple single lenses attached together, at least two of the single lenses including media exhibiting different refractive indices and dispersion.

Compared to conventional relay lens arrangements, such as aspheres and drum lenses, the configuration of this variant has the effect of introducing little aberration or low-angle scattering (which cannot be filtered out).

In a variant, the relay lens arrangement has a diameter within a range of 1.5 to 3.5 mm.

The beam shaping means are dimensioned such that generally all the light passed out is captured by the relay lens. The relatively compact dimensions are unusual for a relay lens arrangement of this configuration, but contribute to the overall compactness of the apparatus.

In an embodiment, the beam shaping means include a generally circular pinhole, providing the aperture, and dimensioned with respect to the beam produced by the device for generating a light beam to generate an Airy pattern in a plane, and a beam stop, positioned in the plane, for blocking secondary maxima of the Airy pattern.

An effect is to provide a beam shaping means with a compact design and relatively good temperature stability. Temperature variations are relatively unlikely to lead to secondary maxima being "missed" by the beam stop. This set-up does not require large lengths of optical fibre and is not as sensitive to geometrical variations due to temperature and/or vibrations as an optical fibre variant. An added effect is that this configuration provides polarisation stability. In a pure monomode fibre beam shaping means, by contrast, the plane of polarisation changes with temperature and stress. The presence of polarisation dependent optical elements such as beam splitters (e.g. for beam power monitoring) and/or mirrors in an optical measurement system means that polarisation stability improves the repeatability of measurements. To achieve polarisation stability with a monomode optical fibre, one has to resort to stress birefringence, which has an adverse effect on the beam circularity and the power distribution in side lobes of the beam's intensity distribution.

In an embodiment, the pinhole is provided in a layer of generally opaque material deposited on a generally transparent substrate of substantially higher thickness than the layer.

As a consequence the pinhole shape is well defined, accurately produced and relatively stable in use so that little aberration is introduced at low manufacturing cost. The layer, supported by the substrate, can be very thin with respect to the diameter of the incident light beam at the pinhole plane. On that scale, the pinhole is shaped less like a cylinder. As a result, there are fewer reflections within this "cylinder", which could act as virtual light sources, leading to aberration of the Airy pattern.

In an embodiment, the pinhole is obtainable by means of a lithographic process.

An effect is that a consistent quality of the pinhole (good circularity) is achievable, in principle determined by the quality of the photolithographic mask (in the case of photolithography) or the electron beam wavelength (in the case of electron beam lithography), and the subsequent etching process.

In an embodiment, at least one of a surface of the substrate carrying the opaque layer and a generally opposite surface of the substrate is positioned at an angle to a direction of propagation of the light beam through the substrate, in use.

An effect is to prevent the light reflected at an interface of the substrate from entering the device that generates the light beam.

An embodiment of the apparatus includes a lens arrangement for, in use, focusing light onto the pinhole.

An effect is to increase the efficiency.

In an embodiment, the lens arrangement includes an assembly of multiple single lenses attached together, at least two of the single lenses including media exhibiting different refractive indices and dispersion.

As a result, relatively little aberration or low-angle scattering is introduced.

In an embodiment, the apparatus is configured such that, in use, the ratio of the $1/e^2$ diameter of the light beam at the pinhole to the pinhole diameter has a value within the range of 3 to 8.

The $1/e^2$ diameter is the diameter corresponding to twice the radial distance from the propagation axis at which the intensity is $1/e^2$ times the intensity on the propagation axis. It has been found that this value gives relatively good results in that the apparatus has sufficient light output for common devices for generating light, but that the sensitivity to misalignments is relatively low. The quality of the transmitted beam in terms of its spatial coherence is diffraction-limited.

According to another aspect, the method of providing a light beam in an optical measurement instrument according to the invention is characterised by passing the beam obtained upon determination of the beam shape and removal of the spatial frequency components through a spatial low-pass filter.

In an embodiment, the method includes the use of an apparatus according to the invention.

According to another aspect, the light scattering instrument according to the invention includes an apparatus for providing a light beam to illuminate a particle sample according to the invention.

The effects provided by the apparatus for providing a light beam come to the fore in a light scattering instrument for determining particle sizes by scattering of light. The apparatus for providing the light beam has a relatively small spatial envelope, leaving space for the sample carrier and sensors. The apparatus provides a beam with high spatial coherence, important for separating scattered light from non-scattered light. The apparatus allows one to re-configure for different wavelengths, unlike a monomode optical fibre filter, which is designed for one narrow wavelength band. Moreover, the polarisation stability of many embodiments of the apparatus for providing a light beam is of benefit, because light scattering is polarisation dependent in the particle size and wavelength range to which Mie scattering theory applies, and because the beam power is generally measured, for which a beam splitter or half-mirror is usually placed in the path of the beam.

The invention will now be explained in further detail with reference to the accompanying drawings, in which.

Figure 1:
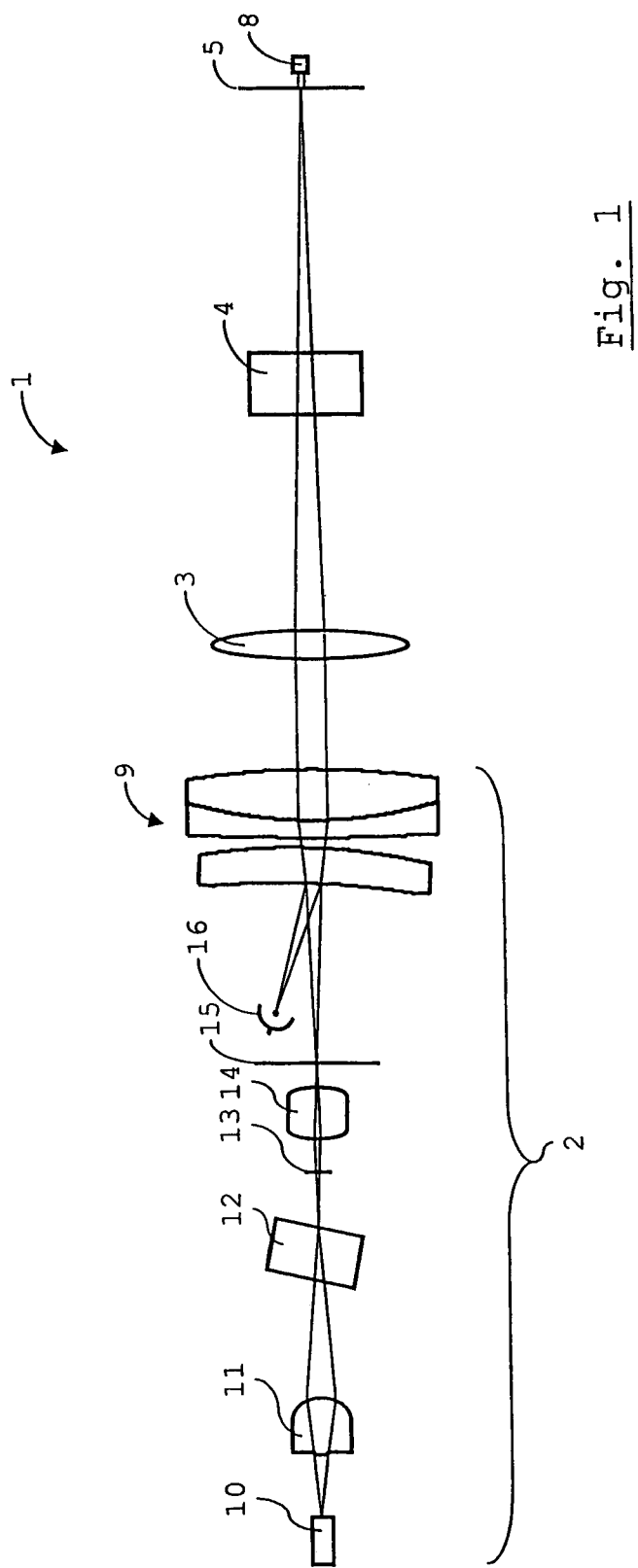
FIG. 1 is a schematic illustration of components of a light scattering instrument, not to scale.
Figure 8:
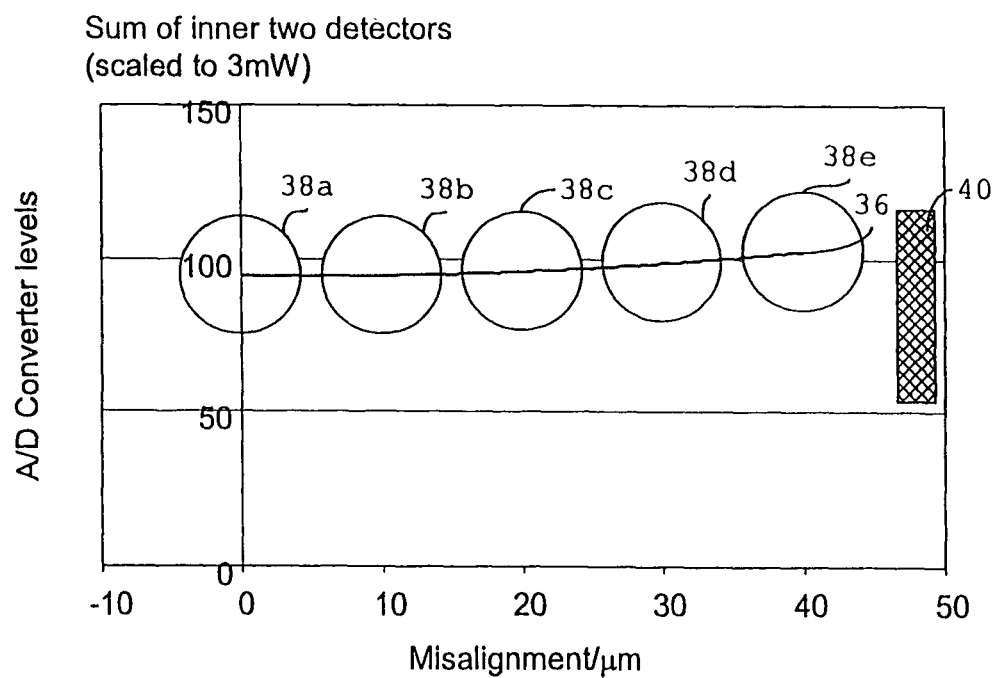
Figure 9:
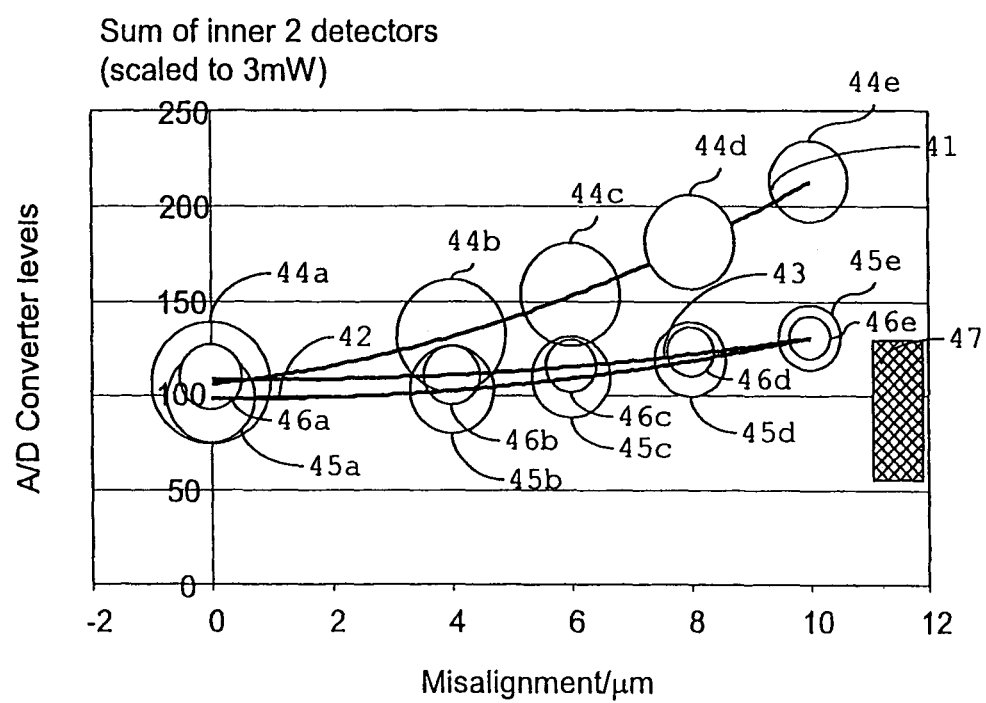

FIG. 8 is a diagram illustrating the sensitivity to misalignments of a beam stop in a first spatial filter in the transverse direction of the light scattering instrument of FIG. 1, with the extra spatial filter present; and FIG. 9 is a diagram illustrating the sensitivity to misalignments of the laser in the transverse direction of the light scattering instrument of FIG. 1 with an extra spatial filter for various pinhole sizes employed to shape the beam.

Figure 2:
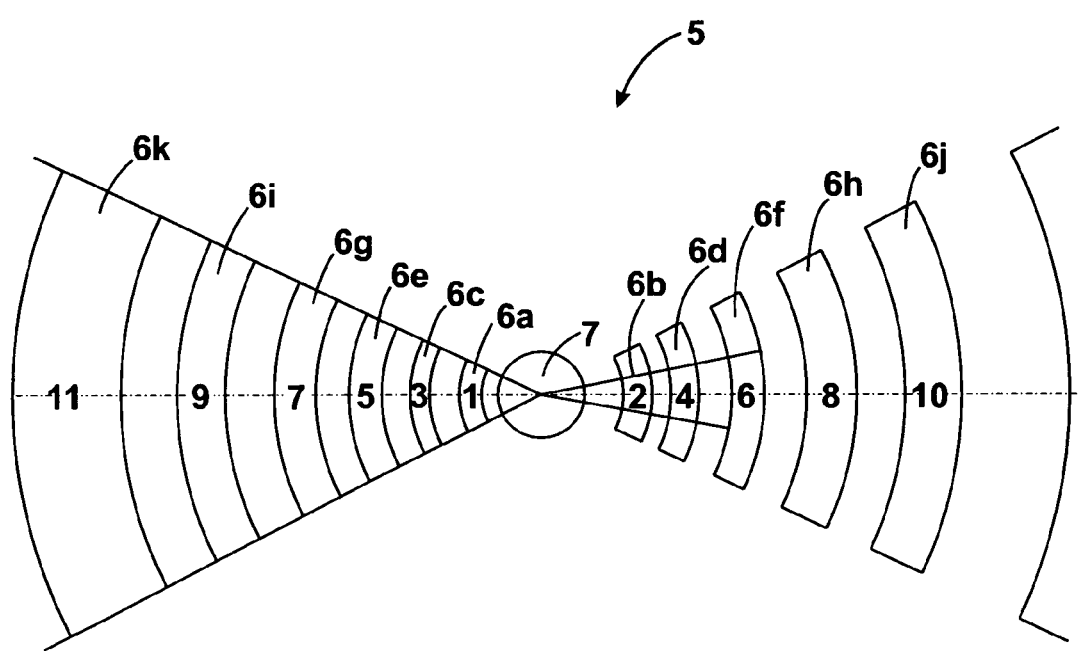
FIG. 2 is a schematic front view of a detector for use in the light scattering instrument.

A light scattering (LS) instrument 1, known also as a laser diffraction instrument, includes an apparatus 2 for producing a beam of spatially coherent light, a range lens 3, a measuring zone 4 and a sensor array 5. The sensor array 5 is positioned generally in the focal plane of the range lens 3. In use, a sample of particles in suspension is introduced in the measuring zone 4. The particles scatter the beam of light in a forward and reverse direction according to an intensity distribution dependent on the particle diameters. Forward-scattered light is detected by sensor segments 6a-6k (FIG. 2) of the sensor array 5. The sensor segments 6a-6k are distributed at increasing radial distances relative to an optical axis generally coinciding with the beam of collimated light. Light that is not scattered passes through a central aperture 7 onto a photosensor 8 for sensing transmission of unscattered light.

It is a requirement of many optical measurements to illuminate a target object with light and to separate the subsequent light scattered from the object from the light that passes through it without being scattered. By this means the instrument is able to discriminate between low angle scattering and the absorption properties of the target that may otherwise be combined. The limit to the separability of the low angle scattering from the unscattered beam is defined by the well-known diffraction limit, which places a lower boundary on the achievable spot size of a focussed beam. The achievement of a "diffraction-limited focussed spot" signifies that the illuminating beam is practically indistinguishable from a perfectly spatially coherent source in use.

The highest spatial coherence that can be practically achieved is therefore replicating this theoretical diffraction limit in an achieved real focus spot. This requires employment of a $TEM_{00}$ beam propagation giving a Gaussian transverse intensity profile to the beam, characterised usually by a $1/e^2$ beam diameter at the focus point. For apertures that are greater than 3-4 times this diffraction-limited $1/e^2$ diameter the power received at the focal plane can be considered negligible from a perfectly spatially filtered beam, allowing these regions to be used for detecting scattered light, in principle.

Real optical systems, however, rarely achieve the diffraction limit to beam spot size, typically because of lens manufacturing imperfections and component form errors. These tend to create aberrations superimposed on the focus spot and cause light power to "leak out" of the main Gaussian spot. This creates some light from the source that is "masking" measurements of scattering from the target object at the angles covered by the aberration.

The light power aberrated out from the main beam could in principle go anywhere in the focal plane at which the laser is focussed, however almost all common aberrations result in leakage of power into the lowest angles of scatter. As a consequence it is the detectors nearest to the beam that record the significant power leakage from an already spatially well-filtered beam.

It should be clear therefore that in such measurements a source having a higher degree of spatial coherence offers improved performance by allowing lower angles of scattered light to be separated accurately from the unscattered beam.

For example in particle size analysis based on angular light scattering, the largest particle size that can be measured in any fixed optical system is determined directly by the smallest angle of scatter that can be measured reliably. Whilst the diffraction-limited spot size sets a fundamental limit to the largest size ever attainable, the presence of aberration in the beam propagation usually imposes a lower achieved limit. Therefore better spatial coherence of the source beam offers real advantages to these optical measurement systems.

The principle of operation of an LS instrument 1 is known as such. Advanced variants will have photodetectors for detecting back-scattered light, and may have additional sources of light at different wavelengths, such as explained e.g. in EP 0 992 785. The present description is concerned with measurements of the forward-scattered light, for which reason such features have been omitted in the drawings.

Forward scattering at low angles by particles can be modelled using Fraunhofer theory as a first approximation. The intensity distribution is governed by $$I = I_0 \left(\frac{x^2}{4}\right)(1+\cos\theta)^2 \left(\frac{J_1(x\sin\theta)}{\sin\theta}\right)^2, \quad x = \frac{\pi d}{\lambda},$$

where $\theta$ is the scattering angle (measured relative to the axis of propagation of the illuminating light beam), $\lambda$ is the wavelength of the illuminating light and d is the particle diameter. $J_1$ denotes a first order Bessel function. In the presence of a sample of particles, an ensemble intensity distribution results, which can be related to a particle diameter distribution using a model embodied in an algorithm executed by a signal processing unit (not shown). In the actual LS instrument 1, the algorithm is based on Mie theory, rather than Fraunhofer theory, but the former reduces to the latter for forward scattering at low angles if the particles are much larger than the wavelength of the illuminating light beam.

From the foregoing equation, it is apparent that large particles scatter less at large angles, and that light with lower wavelengths is scattered at larger angles. It follows that, in order to distinguish between light scattered at low angles by particles at the upper end of the detectable range of particle sizes and light that is not scattered at all, the beam entering the measuring zone 4 must be as spatially coherent as possible. In the present context, this means that the fundamental mode of the beam of light must predominate, and that the light beam must approximate that produced by a point source, i.e. have spherical wavefronts (plane wavefronts in the assymptotic limit). In all embodiments described herein, the assembly of the device for generating a light beam and means for shaping the light beam generated by the device are arranged to produce a light beam with substantially a $TEM_{00}$ profile. Further improvements to the spatial coherence are provided by a further spatial filter that receives the light from the beam shaping means.

From scattering theory, it also follows that light of lower wavelengths scatters at greater angles. There is an advantage in using lower wavelengths, in that it enables the LS instrument 1 to be more compact. The sensor array 5 can, indeed must, be placed closer to the measuring zone 4 if the scattered light subtends a larger angle.

Both Mie and Fraunhofer theory assume that the incident light is spatially coherent. Although the apparatus 2 also finds application in LS instruments using a reverse Fourier set-up, the illustrated example applies a parallel beam of light to the measuring zone 4. To this end, the LS instrument 1 includes a collimation lens assembly 9. The collimation lens assembly 9 will only result in a well-collimated beam if a spatially coherent circular beam with a generally Gaussian intensity distribution is applied to it.

One suitable measure of the spatial coherence of the beam produced by the apparatus 2 is the sum of the intensity values of two innermost sensor segments 6a, 6b of the sensor array 5. This measure will be used herein to demonstrate the effects of the various components of the apparatus 2 and variants thereof, but scaled to correspond to a power output of 3 mW using the signal from the photosensor 8, to take account of different levels of reflective and dissipative losses within the apparatus 2.

The apparatus 2 illustrated in FIG. 1 includes a device 10 for generating a generally monochromatic beam of light, a lens 11 for focusing the light emitted by the device 10 onto a pinhole of a point source generator 12, a first aperture plate, referred to herein as an Airy clipper 13, a relay lens 14, a second aperture plate 15 and a second photosensor 16.

The device 10 for generating a generally monochromatic beam of light may be a light-emitting diode, a solid state laser or a gas laser. The second photosensor 16 is arranged to provide a signal to a control device for controlling the power of the light beam emitted by the device 10. The device 10 is over-dimensioned in the sense that its rated power output is higher than that required to produce an observable intensity distribution at the sensor array 5. Over the lifetime of the apparatus 2, the components may become slightly contaminated and/or misaligned, which would lead to a decrease in the power of the light beam reaching the collimation lens assembly 9. The inner control loop and the over-dimensioning of the device 10 ensure that this decrease does not in actual fact occur. It is a feature of all alternatives to the apparatus 2—described in more detail below—as well.

Figure 3:
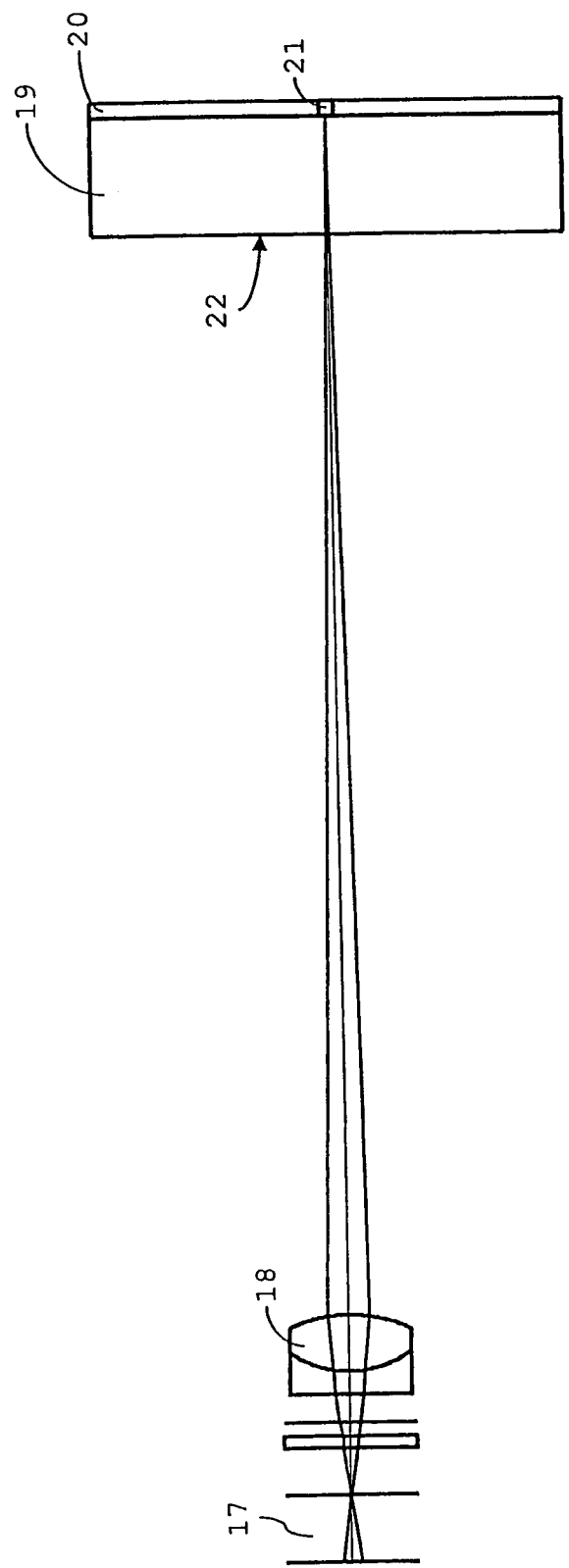
FIG. 3 is a schematic illustration of an embodiment of an apparatus for producing a light beam employing a bulk optic beam shaping means.

FIG. 3 shows an implementation with a laser diode light source 17. In an embodiment, the laser diode light source 17 is configured to emit light with a peak intensity wavelength in the visible range, lower than 500 nm, but preferably around 405 nm. Such blue laser diodes are widely available for use in consumer electronic devices, making them increasingly affordable. The relatively low wavelength ensures that relatively small particles are also within the range of measurement of the LS instrument 1. Of themselves, laser diodes emit light with poor spatial coherence, but this effect is mitigated by the other components of the apparatus 2.

A focusing lens arrangement 18 comprises a doublet: an assembly of two single lenses attached together, made of different types of glass that exhibit different refractive indices and dispersion. An effect is that aberration and noise at low spatial frequencies are generally avoided. This is desirable because the apparatus 2 otherwise comprises only low-pass spatial filters and a beam shaper, so that any such aberrations and noise would remain in the beam used to illuminate the measuring zone 4. The doublet forming the focusing lens arrangement 18 is polished to provide the desired characteristics.

As illustrated in FIG. 3, the point source generator 12 comprises a substrate 19 and a coating 20, in which a pinhole 21 is provided. The pinhole 21 forms a circular aperture, dimensioned, in use, to determine the beam shape emerging from it. That is to say that its diameter is generally smaller than the spot onto which the focusing lens arrangement 18 focuses the beam from the laser diode light source 17. Good results are obtained if the ratio of the $1/e^2$ diameter of the light beam at the pinhole 21 to the pinhole 21 diameter has a value within the range of 3 to 8.

At these dimensions, the pinhole 21 acts as a point source. It is dimensioned with respect to the beam produced by the device 10 for generating a light beam to generate an Airy pattern in a plane in which the Airy clipper 13 is placed. That is to say that the intensity distribution is generally governed by the Airy function:

$$I(\theta) = I(0)\left[\frac{2J_1(ka\sin\theta)}{ka\sin\theta}\right]^2,$$

where $J_1$ denotes the Bessel function of the first order, $\alpha$ denotes the radius of the pinhole 21, and k is the wave number. $\theta$ denotes the angle to the optical axis coinciding with the direction of propagation of the laser beam.

The Airy clipper 13 comprises a light-transmitting aperture in an otherwise opaque plate, sized to coincide with the first minima and therefore block the secondary and all higher order maxima of the Airy pattern. In this way, the Airy clipper 13 is operative to reject spatial frequency components above a certain range in the light beam.

The central maximum of the Airy pattern, the Airy disk, is, to a good approximation, equivalent to a Gaussian, so that the beam emerging from the Airy clipper 13 has substantially a $TEM_{00}$ profile. To produce a near-perfect Airy pattern, the intensity across the pinhole 21 should be about constant. This can be achieved by making the pinhole 21 very small. However, this presents problems in terms of manufacturing tolerances—the pinhole 21 should have good circularity as well—and light throughput. The presence of a spatial filter comprising the relay lens 14 and second aperture plate 15 allows for the requirements of the diameter of the pinhole 21 to be relaxed somewhat.

It is conceivable that, in some embodiments, a pinhole in a metal foil would be used in place of the point source generator 12 described herein in detail. However, the thin coating 20 makes it easier to produce a pinhole 21 with a small extent in the direction of propagation of the laser beam. This further contributes to a well-defined Airy pattern in the plane of the Airy clipper 13.

In one embodiment, the coating 20 is made of nickel. For instance, a nickel foil may be bonded to the substrate 19. In another embodiment, the coating 20 is made of chrome, applied e.g. by vapour deposition to a thickness of 350 nm, for instance. The chrome coating 20 is cheaper to manufacture than a copper or nickel foil. The substrate 19 can be made of fused silica, for instance. Prototypes of the point source generator 12 have been made with pinhole diameters in the range of 6 μm to 18 μm. Because the pinhole 21 determines the beam shape of the apparatus 2, good circularity and accurate sizing are desirable. This is achieved by producing the pinhole 21 by means of a lithographic process, using photolithography or direct electron beam lithography, for instance. A high-quality mask ensures consistently circular pinholes 21 for a series of point source generators 12 manufactured in this way. In one embodiment, the point source generator 12 is manufactured from a larger coated substrate that is cut up into individual point source generators 12. The point source generator 12 is tilted with its normal to a surface 22 opposite the surface supporting the coating 20 at an angle in the range of 1° to 10°, preferably approximately 1.5°, to the optical axis. An effect is that any light reflected at the coating 20 does not return to the laser diode light source 17.

Returning to FIG. 1, the Airy clipper 13 comprises an aperture in a plate of an optically dense material such as copper or nickel. The aperture is typically within the range of 1-2 mm in diameter. It may also be produced using lithographic techniques, or it may be produced by electroforming. The electroforming process reproduces a form with no shrinkage or distortion and does not require a substrate. If the mandrel used in the process has a high quality finish, then the aperture of the Airy clipper 13 will have a high degree of circularity and a diameter within a relatively small tolerance range.

The Airy clipper 13 is followed by a spatial filter comprising the relay lens arrangement 14 and the second aperture plate 15. The relay lens arrangement 14 functions as a Fourier transform lens, forming in its focal plane—where the second aperture plate 15 is positioned—a Fourier transform of the light beam it receives from the beam shaping means comprised of the point source generator 12 and the Airy clipper 13. Higher spatial frequency components of the beam are blocked by the second aperture plate 15.

In the illustrated embodiment, the relay lens arrangement 14 is a custom-polished doublet, like the focusing lens arrangement 18 of FIG. 3. However, the relay lens arrangement 14 has a diameter within a range of 1.5 to 3.5 mm. Instead of a custom-polished doublet, an asphere or a drum lens could have been used. An asphere, which is manufactured in a mould, may, however, introduce low-intensity low-frequency noise. A drum lens could easily introduce aberrations.

The second aperture plate 15 is typically a copper foil with an aperture having a diameter in the range between 10 and 50 µm, preferably about 30-45 µm. The second aperture plate 15 is thin relative to the diameter of the aperture, e.g. by a factor of about eight thinner.

Figure 4:
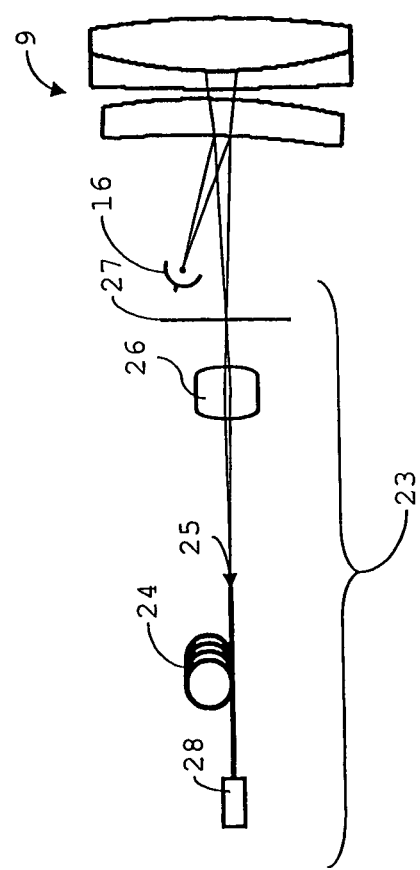
FIG. 4 is a schematic illustration of an embodiment of an apparatus for producing a light beam employing an optical fibre to shape a beam.

FIG. 4 illustrates an alternative, apparatus 23 for producing a light beam for use in the LS instrument 1 instead of the apparatus 2. The alternative apparatus 23 includes an optical fibre 24 dimensioned, in use, to determine the beam shape, and including an aperture 25 from which a spatially filtered laser beam emerges. The optical fibre 24 forms a means for rejecting spatial frequency components above a certain range in the light beam. However, light emerging from the aperture 25 has an intensity distribution according to a Bessel function, for which reason a spatial filter including a relay lens 26 and aperture plate 27 are provided. The optical fibre 24 is shown coupled to a device 28 for generating a beam of monochromatic light, e.g. a laser diode like the laser diode source 17. The relay lens 26 and aperture plate 27 are as the relay lens arrangement 14 and second aperture plate 15 of the embodiment of FIGS. 1 and 3.

As is schematically indicated, the optical fibre 24 is coiled to allow it to have a large length in an otherwise compact instrument. The rejection of cladding modes improves with the length of the optical fibre 24. However, even in a graded-index fibre, there is still a form of aperture 25 resulting in an intensity distribution according to a Bessel function with side lobes, which add distortion to the filtered beam. The embodiment of FIG. 4 is based on the recognition that further improvements cannot be attained by increasing the length of the optical fibre 24, because the aperture 25 imposes a fundamental limit. Instead, the beam quality is further improved by positioning an extra, bulk-optic, spatial low-pass filter after the aperture 25.

A positive effect of the use of both a beam shaping means arranged to reject spatial frequency components above a certain range in the light beam and a spatial filter is that the sensitivity to misalignment is reduced. This is illustrated in FIGS. 5-9, obtained using prototypes of the LS instrument 1 according to FIGS. 1-3.

Depending on the quality of the beam from the collimation lens assembly 9, it will be less or more divergent and exhibit more or less low-angle diffraction in the absence of particles. Therefore, the sum of the incident power on the first and second sensor segments 6a, 6b is a good metric for a comparison, as explained above.

Figure 5:
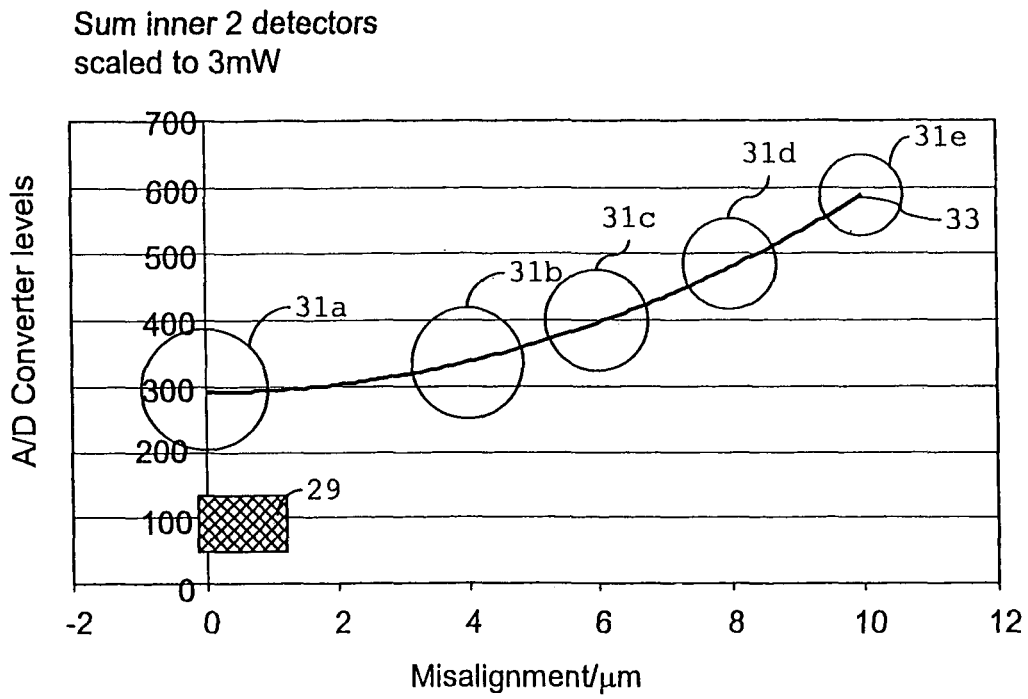
FIG. 5 is a diagram illustrating the sensitivity to misalignments of the laser in the transverse direction of the light scattering instrument of FIG. 1 without an extra spatial filter.
Figure 6:
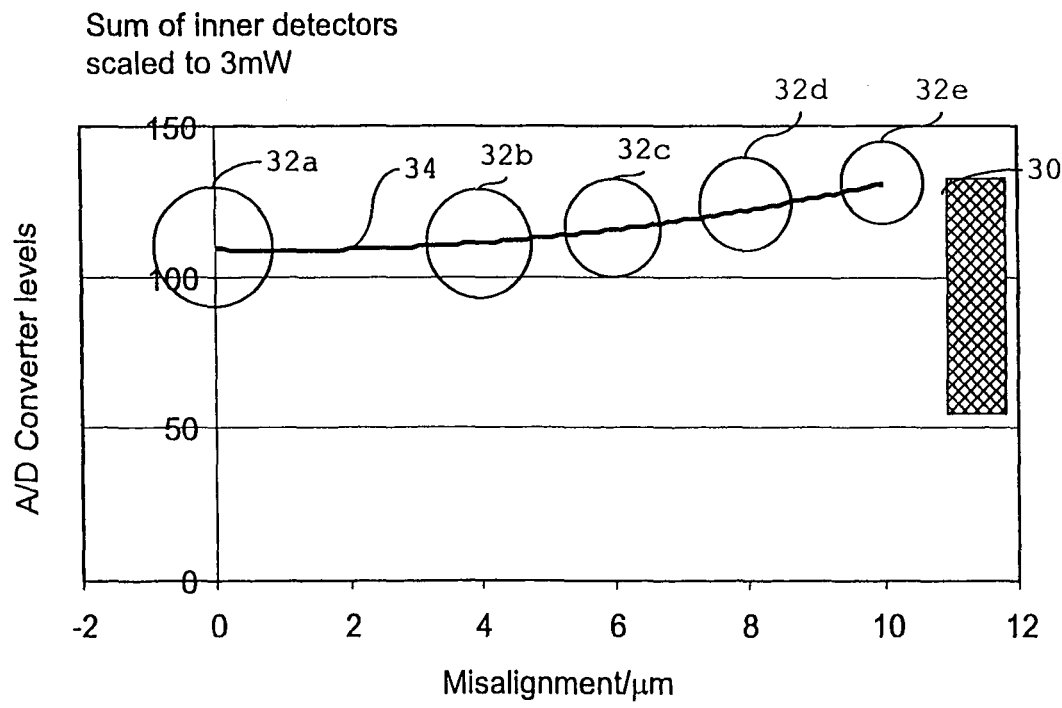
FIG. 6 is a diagram illustrating the sensitivity to misalignments of the laser in the transverse direction of the light scattering instrument of FIG. 1 with an extra spatial filter.

FIG. 5 shows the sum power for a set-up without the spatial filter comprised of the relay lens arrangement 14 and second aperture plate 15. FIG. 6 shows the sum power for exactly the same set-up with a relay lens arrangement 14 and second aperture plate 15. The sum powers have been scaled to take account of attenuation in the relay lens arrangement 14 and differing beam power levels between experiments. The sum power is plotted in terms of the output of an Analogue/Digital converter (not shown) used to discretise photocurrent signals obtained from the sensor array 5.

The diagrams in FIGS. 5 and 6 are based on measurements obtained by varying the distance of the device 10 for generating the light beam to the optical axis of the point source generator 12, Airy clipper 13 and central aperture 7. This misalignment was introduced on purpose using an X-Y stage. It is observed that the sum power measured by both the first and the second sensor segments 6a,6b is plotted because they are positioned at opposite sides of the central optical axis. If only the power incident on one were to be observed, misalignment could lead to an apparent improvement of the observed beam quality.

Hatched regions 29,30 indicate the range of sum power levels obtained by carrying out the same exercise with a state-of-the-art LS instrument for laboratory use comprising a He—Ne gas laser and single bulk optic spatial filter. By contrast the prototype of the LS instrument 1 used a laser diode. The laser of the state-of-the-art instrument was not misaligned: the positions of the hatched regions 29,30 on the x-axis have no meaning. Circles 31a-31e, 32a-32e represent the total beam power from the range lens 3, but are not drawn to the y-axis scale. First circles 31a, 32a correspond to a beam power of 3 mW. It will be clear that the total beam power decreases with increasing misalignment. Furthermore, the total power incident on the inner segments 6a,6b is smaller for the configuration with which FIG. 6 was obtained.

What is also clear, is that the sensitivity to misalignment, represented by the gradients of the graphs 33,34, is smaller when the spatial filter is employed. Moreover, the beam quality is comparable to that of the reference instrument represented by the hatched regions 29,30.

The results of FIGS. 5 and 6 were obtained using a point source generator 12 having a pinhole 21 with a diameter of 8.8 µm, where the coating 20 was made of chrome. The substrate 19 was a substrate in common use for producing photolithographic masks, cut to size and tilted at 2°. The Airy clipper 13 had an aperture with a diameter of 1 mm. The aperture of the second aperture plate 15 had a diameter of 40 µm. The laser diode light source 17 was a 35 mW red laser diode arranged to emit light at a wavelength of approximately 658 nm.

Figure 7:
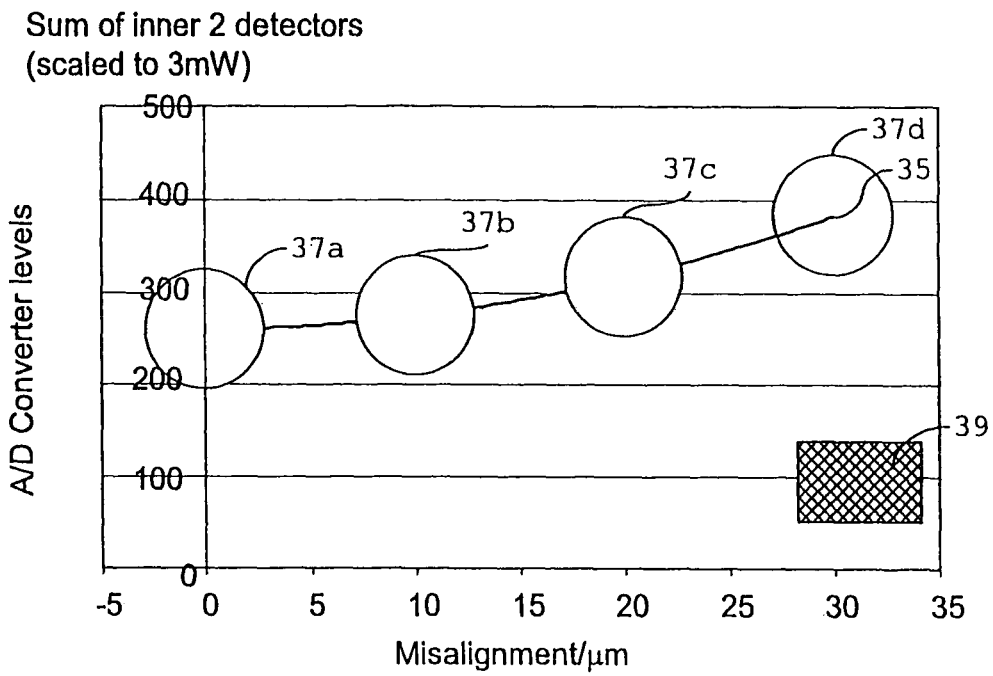
FIG. 7 is a diagram illustrating the sensitivity to misalignments of a beam stop in a first spatial filter in the transverse direction of the light scattering instrument of FIG. 1, but without an extra spatial filter.

FIGS. 7 and 8 show the effects of misalignment of the Airy clipper 13. Again, graphs 35,36 represent the scaled sum of the intensities measured by the inner two sensor segments 6a, 6b. Circles 37,38 represent the absolute laser power. Hatched regions 39,40 represent the sum power for the laboratory instrument used for comparison (without misalignment). Again, it is clear from the slope of the graphs 35,36 that the effect of the spatial filter comprising the relay lens arrangement 14 and second aperture plate 15 is to decrease the sensitivity of the LS instrument 1 to misalignment.

FIG. 9 shows that the spatial filter allows the use of a pinhole 21 with a larger diameter without greatly detracting from the beam quality. This diagram was obtained using the same set-up as used to obtain the diagrams of FIGS. 6 and 8, except that a differently constituted point source generator 12 was used to obtain first, second and third graphs 41,42,43. The laser diode light source 17 was misaligned transversely to the optical axis by the amounts indicated on the x-axis. Again, the graphs 41,42,43 represent the sum intensities scaled to 3 mW beam power. First, second and third circles 44,45,46 represent absolute power levels and a hatched region 47 represents the same reference as the hatched regions 29,30,39,40 in the diagrams of FIGS. 5-8. The first graph 41 and first circles 44 were obtained using a pinhole 21 with a diameter of 17 µm in a copper foil. The second graph 42 and second circles 45 represent measurements obtained with a pinhole 21 with a diameter of 14 µm in a copper foil. The third graph 43 and third circles 46 represent measurements obtained using the same point source generator 12 as was used to obtain FIGS. 5-8.

One can see that it is possible to use the 14 μm pinhole 21 instead of the 8.8 μm pinhole without sacrificing beam quality to the extent that the beam quality is no longer comparable to that in the state-of-the art laboratory instrument. The power levels, indicated by the circles 45, are higher for the pinhole 21 with the larger diameter, which could be desirable, depending on the availability of laser diode light sources 17 with suitable power ratings and on the types of samples to be analysed.

Both the second and third graphs 42,43 demonstrate the low sensitivity to misalignments that characterise the embodiments described herein. The prototype of the LS instrument 1 is also relatively compact, typically less than 160 mm in length along the optical axis.

The invention is not limited to the embodiments described above, which may be varied within the scope of the accompanying claims. For instance, a diode-pumped solid state laser may be used to generate a beam of light with an intensity spectrum peaking at a wavelength value within the visible range. In all embodiments, the devices 10, for generating a beam of light may be implemented as a gas laser, e.g. a Helium-Neon laser. Such lasers comprise an optical cavity formed of a mirror and a half-mirror. Beam wander due to the virtually flat mirrors commonly employed would lead to misalignment problems in use, were it not for the use of the beam shaping means and spatial filter of the apparatuses described herein. In particular, the effects of beam wander are negated to a significant extent where the point source generator 12 is used, because the pinhole 21 is overfilled.

Although this description has focused on an apparatus for providing a light beam for use in a diffraction instrument, it is equally suitable for use in other types of optical measurement instrument for which spatial coherence is important. For example, the apparatus also finds application in the field of optical spectroscopy.

The invention claimed is:

1. Apparatus for providing a diffraction-limited substantially monochromatic light beam for use in a light scattering measurement instrument, the apparatus including
a device for generating a light beam; and
means for shaping the light beam generated by the device, dimensioned, in use, to determine the beam shape, and including
an aperture;
means for rejecting spatial frequency components above a certain range in the light beam, and
further including a spatial low-pass filter arranged to filter a beam provided by the beam shaping means, wherein the spatial low-pass filter includes
a relay lens arrangement, functioning as a Fourier transform lens, and
an aperture plate, positioned generally in a focal plane of the relay lens arrangement.

2. Apparatus according to claim 1, wherein the relay lens arrangement includes an assembly of multiple single lenses attached together, at least two of the single lenses including media exhibiting different refractive indices and dispersion.

3. Apparatus according to claim 2, wherein the relay lens arrangement has a diameter within a range of 1.5 to 3.5 mm.

4. Apparatus according to claim 1, wherein the relay lens arrangement has a diameter within a range of 1.5 to 3.5 mm.

5. Apparatus according to claim 1, wherein the beam shaping means include
a generally circular pinhole, providing the aperture, and dimensioned with respect to the beam produced by the device for generating a light beam to generate an Airy pattern in a plane, and
a beam stop, positioned in the plane, for blocking secondary maxima of the Airy pattern.

6. Apparatus according to claim 5, wherein the pinhole is provided in a layer of generally opaque material deposited on a generally transparent substrate of substantially higher thickness than the layer.

7. Apparatus according to claim 5, wherein the pinhole is obtainable by means of a lithographic process.

8. Apparatus according to claim 5, wherein at least one of a surface of the substrate carrying the opaque layer and a generally opposite surface of the substrate is positioned at an angle to a direction of propagation of the light beam through the substrate, in use.

9. Apparatus according to claim 5, including a lens arrangement for, in use, focusing light onto the pinhole.

10. Apparatus according to claim 9, wherein the lens arrangement includes an assembly of multiple single lenses attached together, at least two of the single lenses including media exhibiting different refractive indices and dispersion.

11. Apparatus according to claim 9, configured such that, in use, the ratio of the $1/e^2$ diameter of the light beam at the pinhole to the pinhole diameter has a value within the range of 3 to 8.

12. A light scattering measurement instrument for determining particle sizes by scattering of light, including an apparatus for providing a light beam to illuminate a particle sample according to claim 1.

13. A method of providing a diffraction-limited substantially monochromatic light beam for use in a light scattering measurement instrument, the method including:
generating a light beam; and
passing the light beam through a passage dimensioned to determine the beam shape and removing spatial frequency components above a certain range from the light beam, which includes passing the beam obtained upon determination of the beam shape and removal of the spatial frequency components through a spatial low-pass filter which comprises a relay lens arrangement functioning as a Fourier transform lens and an aperture plate positioned generally in a focal plane of the relay lens arrangement.

14. A method according to claim 13, including the use of an apparatus according to claim 1.

* * * * *